United States Patent [19]
Brown et al.

[11] Patent Number: 5,603,729
[45] Date of Patent: Feb. 18, 1997

[54] PORTABLE REUSABLE THERMAL THERAPEUTIC DEVICE

[75] Inventors: Blake B. Brown; Charles R. Mason, both of Moberly; Daniel J. Kohout, Columbia, all of Mo.; Joel C. Parrott, Gurnee, Ill.

[73] Assignee: Baxter International Inc., Deerfield, Ill.

[21] Appl. No.: 531,428

[22] Filed: Sep. 21, 1995

[51] Int. Cl.⁶ ........................................ A61F 7/00
[52] U.S. Cl. ................................................. 607/114
[58] Field of Search ............................. 607/114, 104, 607/108, 109, 111

[56] References Cited

U.S. PATENT DOCUMENTS

| | | |
|---|---|---|
| D. 317,571 | 6/1991 | Henriksson . |
| D. 327,329 | 6/1992 | Hubbard et al. . |
| 1,819,807 | 8/1931 | Baysinger . |
| 2,429,973 | 11/1947 | Alexander . |
| 2,759,337 | 8/1956 | Katz . |
| 2,855,758 | 10/1958 | Johnson . |
| 2,907,173 | 10/1959 | Robbins . |
| 2,925,719 | 2/1960 | Robbins et al. . |
| 3,296,819 | 1/1967 | Gough . |
| 3,320,682 | 5/1967 | Sliman . |
| 3,892,905 | 7/1975 | Albert . |
| 3,950,158 | 4/1976 | Gossett . |
| 4,118,946 | 10/1978 | Tubin . |
| 4,289,815 | 9/1981 | Lee . |
| 4,347,848 | 9/1982 | Hubbard et al. . |
| 4,385,950 | 5/1983 | Hubbard et al. . |
| 4,462,224 | 7/1984 | Dunshee et al. ............ 607/114 |
| 4,523,353 | 6/1985 | Hubbard et al. . |
| 4,628,932 | 12/1986 | Tampa . |
| 4,688,572 | 8/1987 | Hubbard et al. . |
| 4,780,117 | 10/1988 | Lahey et al. . |
| 4,951,666 | 8/1990 | Inman et al. . |
| 5,045,041 | 9/1991 | Murphy . |
| 5,062,269 | 11/1991 | Siegel . |
| 5,074,300 | 12/1991 | Murphy . |
| 5,090,409 | 2/1992 | Genis . |
| 5,109,841 | 5/1992 | Hubbard et al. . |
| 5,181,966 | 1/1993 | Honeycutt et al. . |
| 5,184,613 | 2/1993 | Mintz ............................ 607/114 |
| 5,356,426 | 10/1994 | Delk et al. . |

Primary Examiner—Lee S. Cohen
Assistant Examiner—Herman J. Robinson
Attorney, Agent, or Firm—Kay H. P. Hannafan; Robert Stenzel

[57] ABSTRACT

Methods and apparatus are disclosed for the thermal treatment of the body. A first container adapted to receive water is provided. A second container having a substance adapted to react with water and produce a thermal reaction is also provided. The second container is placed inside the first container. At least a portion of the second container is made of a material that at least partially dissolves in water, so as to allow the substance to mix with water and produce the thermal reaction.

17 Claims, 2 Drawing Sheets

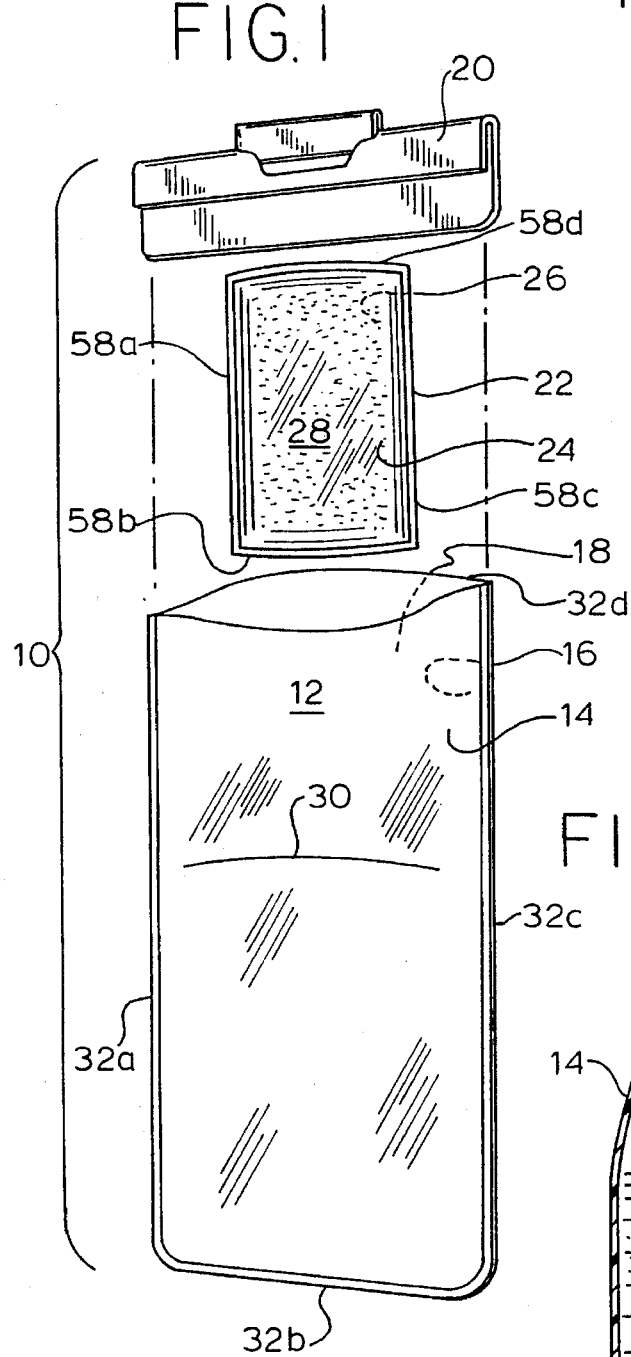
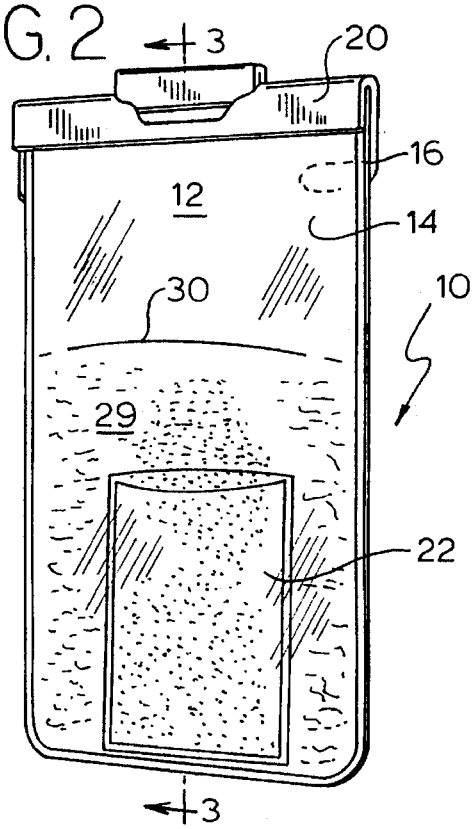
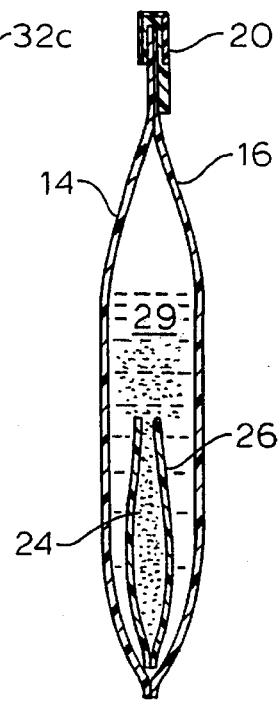
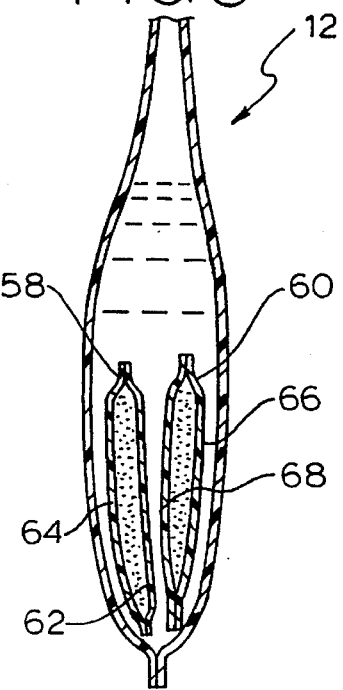

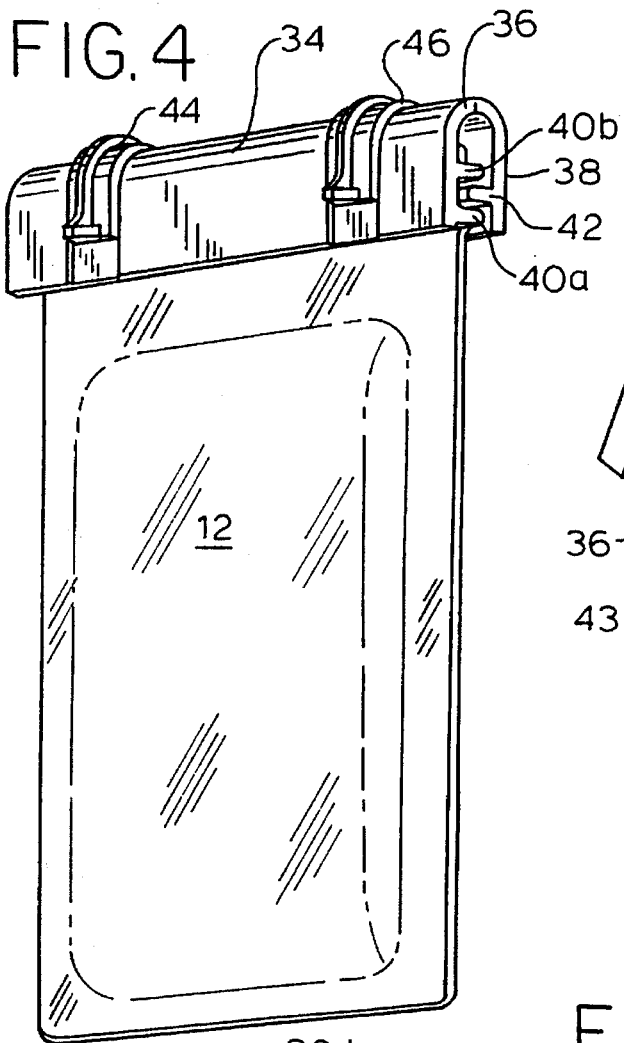
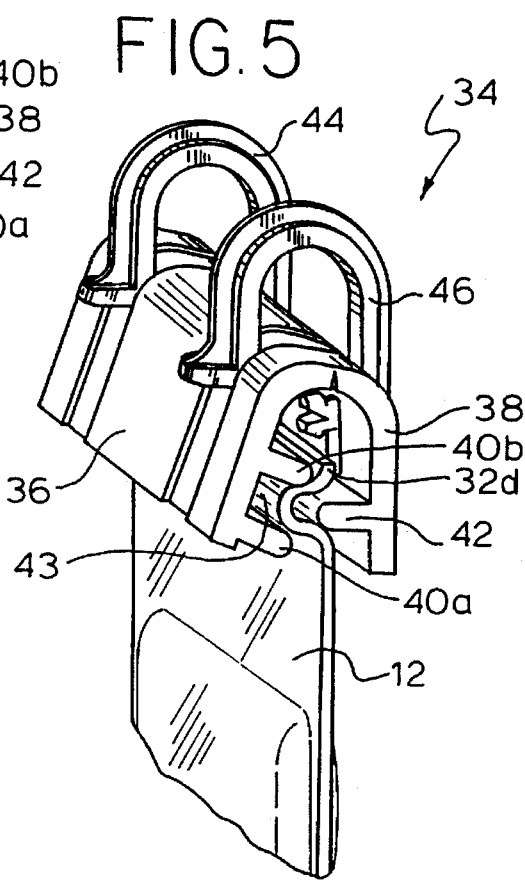
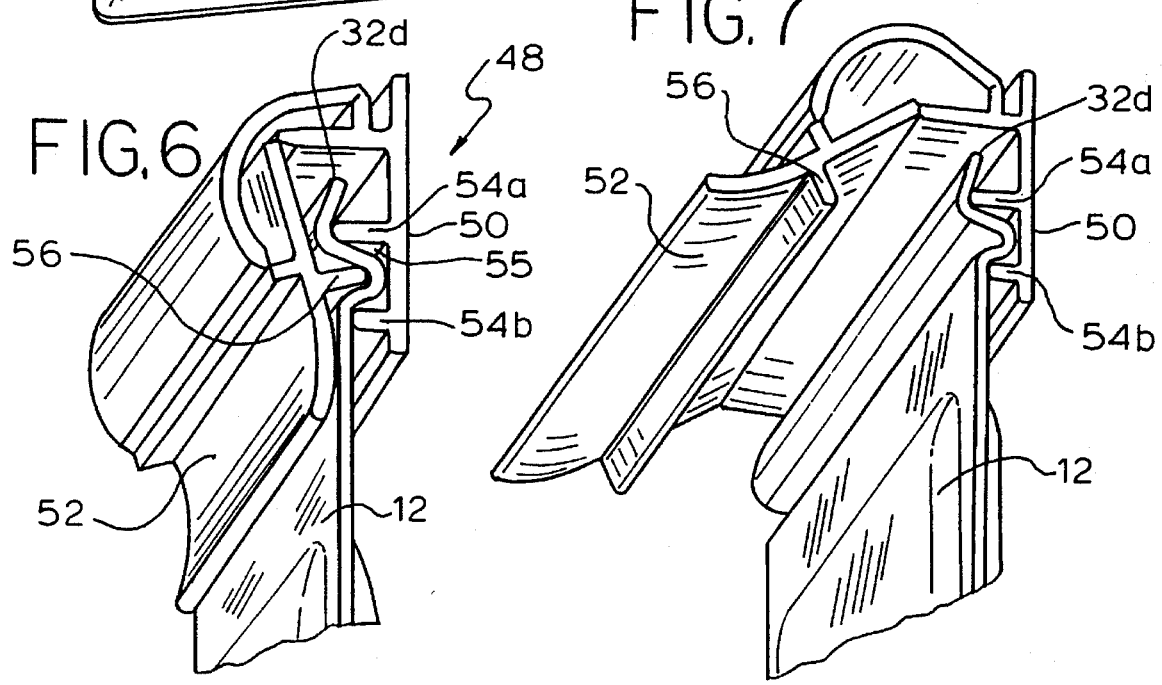
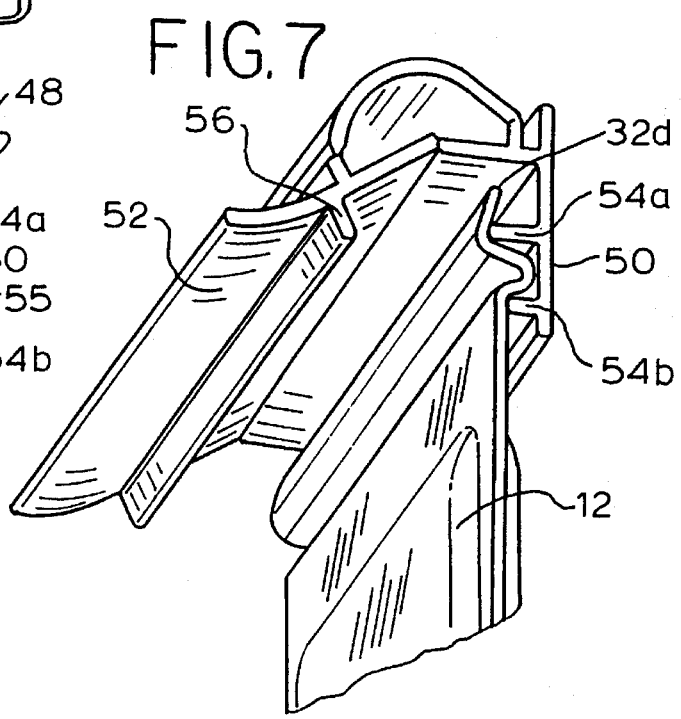

PORTABLE REUSABLE THERMAL THERAPEUTIC DEVICE

BACKGROUND OF THE INVENTION

The present invention relates generally to methods and apparatus for treating injuries. More specifically, the present invention relates to methods and apparatus for the "cold therapy" and/or "heat therapy" of injuries. "Cold therapy" refers to the treatment of injuries such as sprains, knee injuries and the like by directly applying a cold substance (e.g. an ice pack) to the injured area. "Heat therapy" refers to treatment of the body and, more specifically, of muscle strains, stiffness, cramping and the like, by applying a source of heat to the affected part of the body.

In the case of cold therapy, for example, because the swelling associated with the above-described injuries begins almost immediately after the injury has occurred, treatment should begin promptly. Accordingly, it is desirable that whatever the source of cold therapy used for such treatment, the cold therapy source should be readily available, easy to use and capable of providing immediate and effective treatment to the injured area.

The most commonly used cold therapy devices are those that utilize ice as the cooling agent. Such devices typically include a waterproof container filled with ice. In general, the container is filled with ice, sealed and applied to the injured part of the body for a desired period of time. Such ice packs are described, for example, in U.S. Pat. Nos. 4,385,950 and 4,347,848. These patents describe a generally rectangular envelope with a waterproof interior bag located within the envelope. The envelope is open at one end for filling the waterproof interior bag with ice. After the interior bag has been filled with ice, the envelope is sealed and the ice pack applied to the injured area. Other similar ice packs are also described in U.S. Pat. No. 4,628,922 entitled "Knee Ice Pack," U.S. Pat No. 5,109,841 entitled "Facial Ice Pack," U.S. Pat. No. 4,951,666 entitled "Thermal Pack" and U.S. Pat. No. 5,336,426 entitled "Refillable Ice Pack."

The ice packs described above require a readily available supply of ice. If ice is not readily available, then a source of ice must be found and/or the ice transported to the site where the injury occurred. Often, a container that can store ice and keep it from melting must also be provided. Finding, transporting and storing ice makes using such ice packs more cumbersome and less convenient than desired.

Another drawback of using ice as the cooling agent is that stored ice from a freezer may be too cold for use in the "cold therapy" of injuries. For example, it is known that a temperature between approximately 32°–50° F. (0°–10° C.) is preferred for treating injuries of the type described above. Temperatures substantially below 32° F. (0° C.) are not recommended. Indeed, ice having a temperature substantially below 32° F. can, if applied to the injured area for too long, cause frostbite. Ice from a freezer (or other storage container) may often be well below 32° F. (0° C.) and, therefore, too cold for use on an injury for an extended period of time. In addition, ice that is colder than desired may take longer to attain the preferred effective temperature range of 32°–50° F. (0°–10° C.), thereby delaying treatment.

In addition to the cold therapy devices that utilize ice as the cooling agent, the prior art also includes cold therapy devices that do not use ice but, instead, use a chemical reaction to produce the desired temperature for cold therapy. Such devices are commercially available from, for example, the assignee of the present application and are sold under the trade name, Kwik-Kold® and Kwik-Kold® Junior. U.S. Pat. No. 2,907,173 and U.S. Pat. No. 2,925,719 also describe cold therapy devices that utilize a chemical reactant that, when combined with another substance, produces an endothermic reaction and, thereby, reduces the temperature of the cold therapy device.

Cold therapy devices such as those commercially available or described in the above-identified patents are typically prepackaged, with an outer bag and an inner bag. The outer bag contains a chemical reactant such as ammonium nitrate and the inner bag contains water. Ammonium nitrate, when mixed with water, produces the known endothermic reaction

To initiate the endothermic reaction, the water-filled bag is ruptured so as to release the water into the interior of the outer bag. The mixing of water and the ammonium nitrate results in the above-identified endothermic reaction (i.e., the reaction takes energy, in the form of heat, from its surroundings.)

Alternatively, as set forth in the above-identified U.S. Pat. No. 2,907,173, a permanently sealed outer bag may contain two inner bags. A first porous inner bag contains the chemical reactant (e.g. ammonium nitrate) and the second inner bag contains water. Rupturing the second bag releases the water. The porous nature of the first bag (containing the ammonium nitrate) allows the released water to permeate the walls of the first bag, thereby causing the endothermic reaction described above.

U.S. Pat. No. 4,780,117 describes a cold pack wherein granular chemical reactants (e.g. ammonium nitrate) are encapsulated in a material that is at least partially soluble in a liquid. The encapsulated chemical reactant is placed in a first container. A second container filled with the liquid is also placed inside the first container and the first container is then sealed. The second container is physically ruptured to release the liquid. The liquid dissolves the coating applied to the reactant and mixes with the reactant to produce an endothermic reaction.

Finally, U.S. Pat. No. 3,950,158 describes a device that can be used for cold therapy or heat therapy. More specifically, this patent describes a "thermal pack" that includes a multi-bag system wherein a permanently sealed outer bag contains a chemical reactant (e.g. for cold therapy, urea with some ammonium chloride) and an inner bag contains water. To activate the thermal pack, the inner water-filled bag is ruptured to release water into the outer bag and produce a thermal reaction.

The cold therapy devices or thermal packs described above typically utilize an outer bag that is completely sealed. Accordingly, such bags are not reusable and must be disposed of after use. Moreover, because the cold therapy and/or thermal devices or packs are prepackaged with water or other liquid and the chemical reactant, they are heavier and, therefore, less portable and convenient than a device that is not prefilled with water.

Also, storage conditions may affect the performance of these types of devices. For example, in the case of cold therapy, if the entire prepackaged unit has been stored in a warm environment, the temperature of the water or other liquid contained within the inner bag may be higher than desired for the endothermic reaction. If the temperature of the water or liquid is too high, the endothermic reaction may not progress quickly enough or the temperature drop may not be sufficient to reach the desired temperature for cold therapy.

Accordingly, a general object of the present invention is to provide a thermal therapeutic device that does not suffer from the shortcomings described above. (As used herein, the term "thermal therapeutic device" is intended to be generic and include both cold therapy devices and/or heat therapy devices.) Another object of the present invention is to provide a thermal therapeutic device that is inexpensive, more convenient to use and that can, at least in part, be reused. Another object of the present invention is to provide a more lightweight and portable thermal therapeutic device that does not require the user to carry all of the components. A more particular object of the present invention is to provide a multi-container thermal therapeutic device in which one of the containers does not have to be manually ruptured to allow mixing of the contents. These and other objects are also found in the following description of the present invention.

SUMMARY OF THE INVENTION

The present invention is directed to a thermal therapeutic device having an outer container and an inner container disposed within the outer container. The outer container is adapted for receiving a selected amount of water. The inner container includes a selected amount of a substance adapted to react with water to change the temperature of the water. At least a portion of the inner container wall is made of a material which at least partially dissolves upon contact with water to allow the substance to mix with the water and produce a temperature change.

The present invention is also directed to a method for providing a thermal therapeutic device. In accordance with such method, a first container is provided. A second container is also provided. At least a portion of the second container wall is made of a material that at least partially dissolves upon contact with water. A selected amount of a substance is disposed within the second container and the second container is placed within the first container. In accordance with the method of the present invention, a selected amount of water is introduced into the first container. At least a portion of the second container wall dissolves upon contact with the water, and the mixture of water and the substance within the second container results in a change in temperature of the water.

These and other aspects of the present invention are set forth in the following description and the attached drawings.

BRIEF DESCRIPTIONS OF THE DRAWINGS

FIG. 1 is a perspective view of an unassembled thermal therapeutic device embodying the present invention;

FIG. 2 is a perspective view of the assembled thermal therapeutic device of FIG. 1;

FIG. 3 is a cross-sectional view taken along lines 3—3 of FIG. 2;

FIG. 4 is a perspective view of an assembled thermal therapeutic device embodying the present invention using an alternative clamping device;

FIG. 5 is an enlarged perspective view of the clamping device of FIG. 4, in its open condition;

FIG. 6 is an enlarged perspective view of an alternative clamping device in a closed position;

FIG. 7 is an enlarged perspective view of the alternative clamping device of FIG. 6 in an open position;

FIG. 8 is a cross-sectional view of an alternative thermal therapeutic device embodying the present invention.

DETAILED DESCRIPTION OF THE INVENTION

Turning now to the drawings, FIG. 1 shows the thermal therapeutic device 10 of the present invention in its unassembled state. When used for cold therapy, thermal therapeutic device 10 includes an outer container 12 which includes side walls 14 and 16 peripherally sealed along three sides to form interior chamber 18 between side walls 14 and 16. Thermal therapeutic device 10 also includes a sealing device such as, for example, clamp 20 shown in FIGS. 1–3 or, preferably, clamps 34 and 48 in FIGS. 4–7 for sealing the open side of container 12.

Thermal therapeutic device 10 further includes inner container 22. Inner container 22 includes walls 24 and 26 peripherally sealed to define an interior chamber 28 between walls 24 and 26. Interior chamber 28 of inner container 22 is filled with a chemical such as ammonium nitrate.

When it is desired to use the device 10 for cold therapy, water 29 is added to the outer container 12, as shown in FIG. 2. The amount of water required may be indicated on one of the walls 14 or 16 by fill line 30. Inner container 22 may be predisposed in the outer container prior to the addition of water or, preferably, may be added to the outer container 12 after the water has been added. Outer container 12 is then sealed either by clamp 20 or other sealing device.

As set forth in detail below, at least a portion of the wall of the inner container 22 is made of a material that is soluble in water such as polyvinyl alcohol (PVA). Thus, once inner container 22 contacts water, wall(s) 24 and/or 26 or a portion thereof, begins to dissolve, releasing the ammonium nitrate into the water. The ammonium nitrate reacts with the water in accordance with the known endothermic reaction equation:

$$NH_4NO_3 \xrightarrow{H_2O} NH_{4(aq)}^{(+)} NO_{3(aq)}^{(-)}.$$

As the ammonium nitrate mixes with the water, the temperature of the water drops to a temperature suitable for cold therapy. Chemical reactants other than ammonium nitrate, such as urea, ammonium chloride, ammonium persulfate may also be used to produce an endothermic reaction.

After initial treatment, clamp 20 or other sealing means is removed or the container 12 is otherwise unsealed and the contents of outer container 12 disposed of. Once empty, outer container 12 may be immediately reused by refilling outer container 12 with a fresh supply of water and inserting a new inner container 22 in the manner described above. As water is often readily available, the user of the cold therapy device of the present invention need only provide the empty outer container 12 (with clamping device) and the inner container 22 (or a supply thereof) filled with ammonium nitrate. This provides for a lightweight cold therapy device that is, therefore, more portable than the prefilled (with water) disposable cold therapy devices of the prior art.

Turning now more specifically to outer container 12, outer container 12 may be made of any soft pliable or flexible material. The material should be waterproof, leak-proof and pinhole-free. One preferred material for outer container 12 is polyvinyl chloride. Other materials that can be used for outer container 12 include polyesters, polyolefins such as polyethylene (and copolymers thereof), or films such as nylon.

Walls 14 and 16 of container 12 may be made of a single extruded monolayer or, alternatively, a multi-layer coextrudate or laminate. As shown in FIGS. 1 and 2, walls 14 and 16 are peripherally sealed together along three sides, 32a, 32b and 32c by, for example, heat, radio frequency or sonic sealing. Walls 14 and 16 along side 32d are not sealed together and may be pulled apart to open the container. An interior matte finish (not shown) may be provided on the facing film of walls 14 and 16 to facilitate opening of the container 12.

The size of outer container 12, is not critical except that outer container 12 should be large enough to contain the necessary amount of water and the inner container 22 to produce the endothermic reaction. For example, in one embodiment sides 32a and 32c may be between approximately 15–26 cm in length. Sides 32b and 32d may be between approximately 7–15 cm. For strength and puncture resistance, walls 14 and 16 may be between 0.4 and 1 millimeters (mm) in thickness, Preferably, walls 14 and 16 should be between 0.6–0.8 mm in thickness.

As set forth above, open side 32d of outer container 12 is temporarily sealed during use of thermal therapeutic device 10. One way of sealing container 12 at side 32d is to provide a sealing device such as clamp 20 shown in FIGS. 1–3. In general, clamp 20 is placed over walls 14 and 16 along side 32d and compresses side walls 14 and 16 to effectively seal open side 32d.

More preferably, the clamps shown in FIGS. 4–7 may be used to seal open side 32d. For example, as shown in FIG. 4, clamp 34 includes two hinged jaws 36 and 38 between which the open end of outer container 12 is placed. More specifically, hinged jaw 36 includes spaced apart ribs 40a and 40b and hinged jaw 38 includes rib 42 which fits within space 43 between ribs 40a and 40b. The open end of outer container 12 is alternately folded over and under the ribs 40a, 40b and 42 as shown in FIG. 5. As hinged jaws 36 and 38 are brought together into a closed position, ribs 40a, 40b and 42 compress walls 14 and 16 and, thereby, seal the open end of container 12 between ribs 40a and 42 and between ribs 40b and 42. Once container has been sealed, jaws 36 and 38 are locked in place by sliding locking arms 44 and 46 over hinged jaws 36 and 38.

An alternative clamp 48 is shown in FIGS. 6 and 7. Clamp 48 includes a base 50 and hinged cover 52. Base 50 may include at least two spaced apart ribs 54a and 54b. Cover 52 includes rib 56 which fits within space 55 between ribs 54a and 54b. As in the embodiment of FIGS. 4 and 5, the open end 32d of container 12 is folded over (and under) ribs 54a, 54b and 56. Hinged cover 52 is then pressed down toward base 50, thereby causing ribs 54a, 54b and 56 to compress and seal walls 14 and 16 between ribs 54a and 56 and between ribs 56 and 54b. Cover 52 and base 50 may include an automatic locking mechanism, commonly referred to as a "living hinge," wherein downward pressure on cover 52 causes it to securely snap into a closed position. Alternatively, a separate locking mechanism may be used. The clamps described above and shown in FIGS. 4–7 are, preferably, made of a hard plastic such as polypropylene.

Other ways of temporarily sealing open side 32d are also possible. For example, the open end of the container can be rolled or folded repeatedly and clamped. Finally, in lieu of a separate clamp, side 32d of outer container 12 may be sealed by providing a sealing mechanism in walls 14 and 16 such as the commercially known "zip-lock" mechanism.

The clamps shown in FIGS. 1–7 and, in particular, the clamp shown in FIGS. 1–3 are provided for illustrative purposes only and it should be understood that any sealing means which temporarily and effectively seals outer container 12 in a way that allows side 32d to be repeatedly sealed and unsealed can be used.

Turning now to inner container 22, inner container 22 is made, at least in part, of a material that dissolves sufficiently in water to allow mixing of the substance within inner container 22. As used herein, "dissolves" is intended to include any disintegration, decomposition, emulsification, or any other break down of the material, whether by chemical reaction with the water or otherwise. In addition, inner container 22 is made of a material that is suitable for containing a chemical reactant (e.g. ammonium nitrate). One such material is polyvinyl alcohol. As described in U.S. Pat. No. 3,892,905, which is incorporated by reference, polyvinyl alcohol is known to dissolve in water. Other materials such as paper and, more particularly, wax paper or clay and clay-like substances may also be used for inner container 22.

Inner container 22 preferably includes walls 24 and 26 of PVA film, which are peripherally sealed together (by, for example, heat sealing) along sides 58a–58d to form a completely sealed interior chamber for containing a chemical reactant such as ammonium nitrate.

As with the outer container, the size of inner container 22 is not critical provided that the ratio of the ammonium nitrate contained within inner container 22 to water in outer container 12 is sufficient to produce the endothermic reaction and provide a temperature within the effective range (for cold therapy) of 32°–50° F. For example, the cold therapy device of the present invention may include, by weight, between about 30%–70% water and about 30%–70% ammonium nitrate and, more preferably, about 40%–50% water and about 50%–60% ammonium nitrate. Government regulations, if any, regarding the use and disposal of ammonium nitrate may also be considered when determining the amount of ammonium nitrate to be used. For ease of disposal in accordance with such regulations, the cold therapy device of the present invention may include about 56%–64% water and about 36%–44% ammonium nitrate and, more specifically, about 60% water and 40% ammonium nitrate. For purposes of illustration only, in one embodiment, outer container 12 may have sides 32a and 32c that are between 15–26 centimeters in length and sides 32b and 32d that are 7–15 centimeters. Inner container 22, which is filled with ammonium nitrate, may have sides 58a and 58c that are approximately 7–10 centimeters in length and sides 58b and 58d that are 6–9 centimeters.

The thickness of walls 24 and 26 of inner container 22 is selected based on the desired length of the endothermic reaction, but is most typically between 0.01–0.1 mm, and preferably 0.02–0.08 mm for a cold therapy procedure that is approximately 30–45 minutes in duration. If, however, it is desired that the reaction be prolonged or proceed at a slower rate, the walls 24 and 26 of inner container 22 may be slightly thicker to allow for slower dissolving of the PVA and, thereby, the slower mixing of ammonium nitrate with water. (A thicker wall may be provided by, for example, laminating two sheets of PVA film or by extruding a thicker single sheet of PVA film). On the other hand, if it is desired that the effective range be quickly attained, walls 24 and 26 may be thinner so as to allow for quicker dissolution of the PVA film in water and, thereby, faster mixing of ammonium nitrate with water.

Alternatively, as shown in FIG. 8, a prolonged reaction may also be attained by providing two inner containers 58 and 60, each containing ammonium nitrate and having walls or wall portions of varying density and/or thickness. For example, walls 62 and 64 of first inner container 58 may be thinner or less dense than walls 66 and 68 of second inner container 60 to allow walls (or portions thereof) of first inner container 58 to dissolve more quickly than walls 66 and 68 of second inner container 60. More particularly, the thickness of first inner container walls 62 and 64 may be near the lower end (e.g. 0.01 mm) of the above-described thickness range and the thickness of second inner container walls 66 and 68 may be near the upper end (e.g. 0.1 mm) of the above-described range. Thus, the ammonium nitrate in container 58 is released and reacts with the water before the walls of container 60 are completely dissolved. As the walls of second inner container 60 dissolve, additional ammonium nitrate is released, thereby prolonging the endothermic reaction. A suitable amount of water relative to the total amount of ammonium nitrate in both inner containers should also be provided in accordance with the water/ammonium nitrate ratios set forth above.

The ammonium nitrate used (for cold therapy) in the thermal therapeutic device 10 of the present invention may be provided in pellet or a finer granular or even powdery form. Ammonium nitrate suitable for use in the thermal therapeutic device 10 of the present invention is commercially available from Mississippi Chemical Company of Yazoo City, Miss. or Cominco Chemicals and Fertilizers of Spokane, Wash.

PVA is a known compound that is available from various different sources. For example, suitable PVA films known as QA2000 or QA2004 are available from Polymer Films Inc. of Rockville, Conn. Another suitable and, in fact, preferred PVA film is known as Hi-Selon C-200 available from Nippon Gohsei U.S. Company of New York, N.Y.

It has been found that PVA film immersed in water dissolves anywhere between about 1–60 seconds. For standard use in cold therapy (i.e. where a prolonged reaction is not desired), it is preferred that the PVA container dissolve as quickly as possible, preferably, in under 40 seconds and ideally in approximately 15 seconds or less. Typically, the PVA inner container used in the present invention dissolves between 30–40 seconds. Faster dissolution of the PVA container may be achieved (e.g. less than 15 seconds) if the PVA inner container is agitated slightly in the water. A colored dye may be included in the PVA or added separately to the thermal therapeutic device to indicate when most or all of the PVA has dissolved.

As soon as the PVA film begins to dissolve, and the ammonium nitrate begins to mix with the water, the temperature of the water begins to fall and approach the effective range for cold therapy. If the starting temperature of water is less than 50° F. (10° C.) and, thus, already within the effective temperature range for cold therapy, temperatures near 32° F. (0° C.) may be attained (with a suitable proportion of ammonium nitrate to water) in 2–3 seconds. If the water temperature is at or near, for example, 70° F. (21° C.), the water may reach temperatures near 32° F. (0° C.) in approximately 30–90 seconds.

Of course, it must be understood that other factors, such as the thickness of the PVA film, the amount of water, the amount of ammonium nitrate, the ratio of water to ammonium nitrate and whether the PVA container has been agitated may also affect the progress of the endothermic reaction. However, unlike the prepackaged cold therapy devices of the prior art, water is not typically stored in the outer container of the cold therapy device of the present invention, but is added to the outer container immediately before use of the cold therapy device. Accordingly, because a source of cool or cold water is almost always readily available, the temperature of the water should not usually be a limiting factor in the present invention.

Cold therapy "procedures" typically last between 30–45 minutes. With the present invention, however, it has been shown that the effective temperature range of 32°–50° F. (0–10°) can be maintained, if necessary, for up to 60 minutes. It should be understood, however, that the ability to maintain the effective temperature range may also depend, in part, on some of the factors discussed in the preceding paragraph (e.g. starting temperature of the water, amount of ammonium nitrate etc.).

The thermal therapeutic device 10 of the present invention may also be used for heat therapy. When used for heat therapy, the thermal therapeutic device 10 also includes outer container 12 and inner container 22 as described above. As in the cold therapy device described above, at least a portion of inner container wall 24 and/or 26 is made of a material that at least partially dissolves in water (e.g. polyvinyl alcohol). Inner container 22 contains a chemical reactant that when mixed with a liquid (e.g. water) produces an exothermic reaction. One such reactant is sodium acetate or the salt of sodium acetate (i.e. acetic acid sodium salt). Other reactants that may be used for heat therapy include magnesium sulfate and calcium chloride.

In general, the effective range for heat therapy is about 100° F. (38° C.) to 115° F. (46° C.) and, more preferably, 104° F. (40° C.) to 110° F. (43° C). Using the salt of sodium acetate as the chemical reactant, temperatures within the above-described preferred effective temperature range can be obtained when the thermal therapeutic device includes, by weight, approximately 45% to 50% of sodium acetate salt and 50–55% water, with 47.5% sodium acetate salt and 52.5% water being preferred.

Although the present invention has been described in various embodiments (including preferred embodiments), it will be appreciated by those of ordinary skill that various modifications and changes may be made without departing from the present invention as set forth in the appended claims.

That which is claimed:

1. A thermal therapeutic device comprising an outer container and an inner container disposed within said outer container:

said outer container comprising at least one wall defining an interior chamber, said interior chamber being adapted for receiving a selected amount of water, said outer container having a resealable opening;

said inner container comprising at least one wall defining an interior chamber and a predetermined amount of a substance disposed within said interior chamber, said substance adapted to react with water to change the temperature thereof;

whereby at least a portion of said inner container wall comprises a material that at least partially dissolves upon contact with water to allow said substance disposed within said inner container to mix with water added to said outer container to produce a temperature change; and whereby said water and said substance can be discharged from said outer container through said opening and a fresh supply of water and a new inner container can be introduced through said opening and said opening resealed for repeated use.

2. The thermal therapeutic device of claim 1 wherein said outer container includes a selected amount of water within its interior chamber.

3. The thermal therapeutic device of claim 1 wherein said material that at least partially dissolves upon contact with water comprises polyvinyl alcohol.

4. The thermal therapeutic device of claim 2 wherein said substance adapted to react with water comprises ammonium nitrate.

5. The thermal therapeutic device of claim 4 wherein the combination of ammonium nitrate and water comprises by weight, between 36%–44% ammonium nitrate and 56%–64% water.

6. The thermal therapeutic device of claim 3 wherein said polyvinyl alcohol wall portion has a thickness of between 0.01–0.1 mm.

7. The thermal therapeutic device of claim 1 wherein said substance adapted to react with water comprises the salt of sodium acetate.

8. The thermal therapeutic device of claim 3 comprising a first inner container and a second inner container, each including a wall portion comprising polyvinyl alcohol, wherein said second inner container wall portion is thicker than the first inner container wall portion.

9. A method for providing a thermal therapeutic device comprising:

(a) providing a first container comprising at least one wall defining an interior chamber and a resealable opening between the outside environment and said interior chamber;

(b) providing a second container comprising at least one wall defining an interior chamber and a selected amount of a substance disposed within said interior chamber, said substance adapted to react with water and change the temperature thereof;

at least a portion of said second container wall comprising a material that at least partially dissolves in water;

(c) disposing said second container within the interior chamber of said first container; and (d) introducing a selected amount of water into said interior chamber of said first container;

(e) sealing said opening in said first container;

(f) allowing said water to mix with, said substance;

(g) unsealing said opening; and (h) discharging said water and said substance through said opening.

10. The method of claim 9 further comprising disposing said second container within said interior chamber of said first container before introducing a predetermined amount of water into the interior chamber of said first container.

11. The method of claim 9 further comprising disposing said second container within said interior chamber of said first container after introducing a predetermined amount of water into the interior chamber of said first container.

12. The method of claim 9 further comprising the step of agitating said containers to accelerate the mixing of said substance with water.

13. The method of claim 9 further comprising repeating steps (b)–(d) of claim 9.

14. The method of claim 9 wherein said substance comprises ammonium nitrate.

15. The method of claim 9 wherein said material that at least partially dissolves in water comprises polyvinyl alcohol.

16. The method of claim 14 wherein the combination of ammonium nitrate and water comprises by weight between 36–44% ammonium nitrate and 56–64% water.

17. The method of claim 9 wherein said substance comprises the salt of sodium acetate.

* * * * *